US010614567B2

(12) United States Patent
Tiwari et al.

(10) Patent No.: US 10,614,567 B2
(45) Date of Patent: Apr. 7, 2020

(54) QUANTIFYING MASS EFFECT DEFORMATION WITH STRUCTURAL RADIOMICS IN BRAIN TUMOR PATIENTS

(71) Applicant: Case Western Reserve University, Cleveland, OH (US)

(72) Inventors: Pallavi Tiwari, Shaker Heights, OH (US); Anant Madabhushi, Shaker Heights, OH (US); Gavin Hanson, Cleveland Heights, OH (US); Jhimli Mitra, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 452 days.

(21) Appl. No.: 15/397,854

(22) Filed: Jan. 4, 2017

(65) Prior Publication Data

US 2018/0025489 A1 Jan. 25, 2018

Related U.S. Application Data

(60) Provisional application No. 62/366,325, filed on Jul. 25, 2016.

(51) Int. Cl.
*A61B 5/05* (2006.01)
*G06T 7/00* (2017.01)
(Continued)

(52) U.S. Cl.
CPC .......... *G06T 7/0012* (2013.01); *A61B 5/0037* (2013.01); *A61B 5/0042* (2013.01);
(Continued)

(58) Field of Classification Search
CPC .. A61B 5/055; A61B 2576/026; A61B 5/0037
See application file for complete search history.

(56) References Cited

U.S. PATENT DOCUMENTS 5,926,568 A 7/1999 Chaney et al.
2012/0280686 A1* 11/2012 White .............. G01R 33/56341
324/309

FOREIGN PATENT DOCUMENTS

WO 2015138385 A1 9/2015

OTHER PUBLICATIONS

Pizer, et al. "Segementation Registration and Measurement of Shape Variation Via Image Object Shae." IEEE Transactions on Medical Imaging, vol. 18, No. 10, Oct. 1, 1999, pp. 851-865.
McInerney, et al. "Deformable Models in Medical Image Analysis." Proceedings of the IEEE Workshop on Mathematical Methods in Biomedical Image Analysis, Jun. 21, 1995, pp. 171-180.
(Continued)

*Primary Examiner* — Michael J D'Abreu
(74) *Attorney, Agent, or Firm* — Eschweiler & Potashnik, LLC

(57) ABSTRACT

Methods and apparatus quantify mass effect deformation in diagnostic images of patients demonstrating glioblastoma multiforme (GBM). One example apparatus includes an image acquisition circuit that acquires an image of a region of tissue demonstrating GBM pathology, a delineation circuit that segments a tumor region from the image, a pre-processing circuit that generates a pre-processed image by pre-processing the segmented image, a registration circuit that registers the pre-processed image with a template image of a healthy brain, a deformation quantification circuit that computes a set of differences between a position of a brain sub-structure represented in the registered image relative to the position of the brain sub-structure represented in the template image. Embodiments may include a classification circuit that classifies the region of tissue as a long or short-term survivor based, at least in part, on the set of differences.

14 Claims, 12 Drawing Sheets

(51) Int. Cl.
   *A61B 5/00* (2006.01)
   *G06T 7/11* (2017.01)
   *A61B 5/055* (2006.01)
   *A61K 49/06* (2006.01)
   *G01R 33/56* (2006.01)

(52) U.S. Cl.
   CPC ............ *A61B 5/055* (2013.01); *A61B 5/7246* (2013.01); *A61B 5/7282* (2013.01); *A61K 49/06* (2013.01); *G01R 33/5601* (2013.01); *G01R 33/5602* (2013.01); *G01R 33/5608* (2013.01); *G06T 7/11* (2017.01); *A61B 2576/026* (2013.01); *G06T 2207/10088* (2013.01); *G06T 2207/30016* (2013.01)

(56) References Cited

OTHER PUBLICATIONS

Rockne, et al. "Predicting the Efficacy of Radiotherapy in Individual Glioblastoma Patients in Vivo: A Mathematical Modeling Approach; Predicting Efficacy of Radiotherapy in Gliomas." Physics in Medicine and Biology, Institute of Physics Publishing, Bristol GB, vol. 55, No. 12, May 18, 2010, pp. 3271-3285.

Gooya, et al. "Deformable Registration of Glioma Images Using EM Algorithm and Diffusion Reaction Modeling." IEEE Transactions on Medical Imaging, vol. 30, No. 2, Feb. 1, 2011, pp. 375-390.

International Search Report & Written Opinion of the International Searching Authority dated Sep. 18, 2017 for International Application No. PCT/US2017/042396.

\* cited by examiner

QUANTIFYING MASS EFFECT DEFORMATION WITH STRUCTURAL RADIOMICS IN BRAIN TUMOR PATIENTS

CROSS REFERENCE TO RELATED APPLICATIONS

This application claims the benefit of U.S. Provisional Application 62/366,325 filed Jul. 25, 2016.

BACKGROUND

Glioblastoma multiforme (GBM) is the most common primary brain tumor in adults. GBM is characterized by a high proliferative rate and aggressive invasiveness within the brain. Patients diagnosed with GBM may be subjected to aggressive multimodal treatment including surgery, radiotherapy, or chemotherapy. Despite aggressive multimodal treatment, the median survival time after diagnosis for GBM patients ranges from ten to fourteen months. However, individual outcomes are very heterogeneous, with five percent to ten percent of patients diagnosed with GBM being long-term survivors who survive for more than three years.

Within the confined environment of the brain vault, tumor growth, especially in aggressive cancers such as GBM, forces the compression of surrounding brain tissue. This compression results in increased intracranial pressure, exacerbation of vasogenic edema, and brain herniation. Herniation or gross distortion of the brain stem is the cause of death in approximately 60% of GBM cases.

Some conventional approaches to predicting GBM survival times attempt to identify prognostic markers, including tumor size, location, age, or Karnofsky performance scores (KPS). Other approaches attempt to associate molecular markers with survival time. While some prognostic markers have been identified as indicative of GBM survival time, outcomes remain heterogeneous. Furthermore, molecular heterogeneity within GBM tissue represents a challenge to the development of targeted GBM therapies.

Conventional radiomic analysis approaches to predicting GBM survival time have confined their analysis to within GBM tumor or peri-tumoral areas. Other conventional approaches for predicting GBM survival time attempt to identify a relationship between the extent of tumor mass effect as manifested on magnetic resonance imaging (MRI) images and overall survival time. These conventional approaches use 2-dimensional (2D) distance-to-the-midline measurements to capture midline shift due to mass effect. However, conventional approaches that use simplistic 2D distance-to-the-midline measurements provide conflicting and ambiguous results. Since radiologists may be challenged to reliably distinguish long-term survivors from short-term survivors using conventional approaches in clinically relevant time frames, patients may be subjected to sub-optimal treatments. These treatments may take time, cost money, and put a patient at additional risk.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
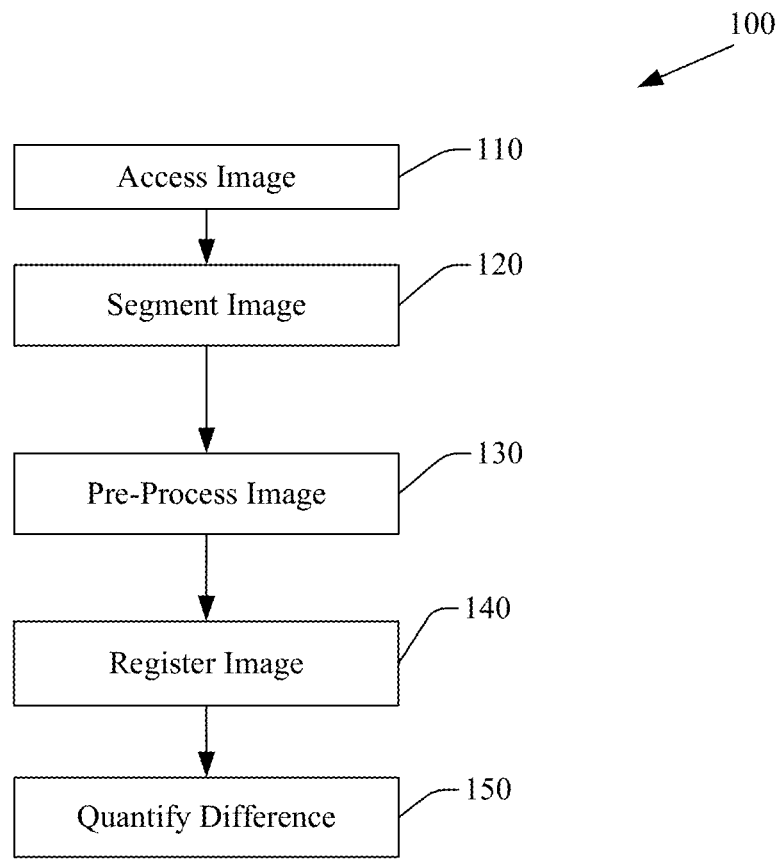
FIG. 1 illustrates an example method for quantifying deformation in an image of a region of tissue demonstrating GBM.

GBM is a rapidly growing brain tumor that causes mass effect and edema in surrounding brain areas. GBM is associated with median survival times of approximately fourteen months for patients diagnosed with GBM. Mass effect has an impact on different substructures in the brain, and this impact may be represented on treatment-naïve MRI. Mass effect, as manifested on anatomical MRI images of the brain, differentially deforms neighboring structures in the brain, leading to significantly higher deformations in patients with more aggressive GBM compared to patients with less aggressive GBM. However, subtle tissue deformations caused by mass effect are often not visible to human readers and may cause progressive neurological deficits, thus impacting GBM survival. Therefore, a more accurate and timely approach to predicting GBM survival that detects sub-visual features demonstrated on anatomical MRI that was also not subject to intra-reviewer variability would be beneficial.

Example methods and apparatus extract radiomic (e.g., computer extracted) features from a radiological image of a region of tissue demonstrating GBM, capture a deformation of the region of tissue relative to a healthy brain, and quantify the deformation. In one embodiment, example methods and apparatus may quantify the deformation by computing a mass effect deformation heterogeneity (MEDH) for the region of tissue. In another embodiment, example methods and apparatus may quantify the deformation by computing a level of cerebrospinal fluid contraction or expansion using tensor-based morphometry (TBM). Example methods and apparatus may associate the quantified deformation (e.g., MEDH) with GBM survival times in a population. Example methods and apparatus may also predict survival time for the patient from whom the radiological image was extracted based, at least in part, on the quantified deformation.

Example methods and apparatus access a diagnostic image of a patient demonstrating GBM. The image may be a gadolinium (Gd) contrast T1w, T2w, or fluid attenuated inversion recovery (FLAIR) MRI image of a patient demonstrating GBM. In other embodiments, other image acquisition parameters may be employed.

Example methods and apparatus may segment a combined tumor area from a diagnostic image of a region of tissue of a patient demonstrating GBM before computing differences between the diagnostic image and a healthy template image or atlas. The combined tumor area may include a necrotic core region, an active region, and an edema region. Segmenting the combined tumor area from the rest of the image before computing similarity measures ensures the exclusion of intensity differences within the combined tumor area. Segmenting the combined tumor area also ensures that example methods and apparatus may consider only the spatial intensity differences due to structural deformation cause by mass effect when compared to the corresponding healthy template or atlas. The combined tumor area may be segmented manually, or may be segmented automatically. For example, the combined tumor area may be segmented using Glioma Image Segmentation and Registration (GLISTR) or other deep learning segmentation approaches. Example methods and apparatus may pre-process the segmented diagnostic image. Pre-processing may include bias field correction, intensity standardization, or skull stripping. Example methods and apparatus may bias field correct the segmented diagnostic image for intensity inhomogeneity induced by bias of the magnetic head coil using an N4 bias correction approach. Example methods and apparatus may normalize the segmented diagnostic image using a histogram matching approach that may include, in one embodiment, 255 bins and 64 points. Example methods and apparatus may skull strip the segmented diagnostic image using non-rigid alignment with an atlas of normal or healthy brain imagery. One atlas suitable for use with example embodiments is a T1w Montreal Neurological Institute (MNI) atlas. Skull stripping may be used to obtain a patient-specific brain mask by non-rigidly aligning the atlas of normal or healthy brain imagery with the diagnostic image. In another embodiment, a set of pre-operative radiological images may also be pre-processed in a similar manner.

Example methods and apparatus capture deformations between the diagnostic image and a healthy brain image by registering the pre-processed diagnostic image with the healthy brain image or images. Registering the pre-processed diagnostic image with a healthy brain image may include registering the pre-processed diagnostic image with the atlas of MRI images using a diffeomorphic registration approach. Example methods and apparatus may employ deformable registration to register the diagnostic image with the healthy template. For example, Advanced Normalization Tools (ANTs) Symmetric Normalization (SyN) may be employed. SyN diffeomorphic registration maps brain structures in the diagnostic image to a healthy template in the presence of brain lesions, including GBM. ANTs maps a tumor-exclusive region using a constrained cost-function approach that is determined by a solution of a negative tumor mask region. In another embodiment, other registration approaches may be employed. For example, example methods and apparatus may employ GLISTR to register an image with the template. GLISTR is a tumor-aware registration tool that is driven by healthy tissue and tumor tissue segmentations obtained from multi-parametric MRI.

Example methods and apparatus quantify differences between the diagnostic image with the healthy brain image or atlas captured by the registration process. In one embodiment, example methods and apparatus compute an MEDH for the region of tissue. In another embodiment, example methods and apparatus may quantify the deformation by computing a level of cerebrospinal fluid contraction or expansion using a tensor-based morphometry (TBM) approach.

Computing MEDH for the region of tissue includes computing a voxel-wise deformation for the region of tissue demonstrating GBM represented in the MRI image. The voxel-wise deformation may be computed as a deformation field-vector in three planar orientations. Example methods and apparatus may compute a Euclidean norm of the scalar values of the deformation orientations represented by the deformation field-vector to obtain a magnitude of deformation per-voxel.

MEDH may be associated with survival time for patients demonstrating GBM. Example methods and apparatus correlate the MEDH with overall GBM survival time of a population of patients demonstrating GBM, where a member of the population demonstrates a primary tumor on either the right or left cerebral hemisphere. Higher variations in tissue deformation within the functionally eloquent and memory areas of the contralateral cerebral hemisphere are related to decreased survival time of GBM patients. Example methods and apparatus may statistically associate MEDH with patient survival time separately for right hemispheric or left hemispheric tumors. Statistically associating MEDH with different hemispheric tumors facilitates computing the effect of deformation due to tumor presence in contralateral hemispheres when performing a group-wise analysis. By excluding tumor areas from the computation of similarity measures for deformable alignment, the magnitude of deformation within tumor regions is close to null. Thus, for patient groups with right cerebral GBM, the deformations are more accurately interpreted within the contralateral left-hemispheric functional areas and in areas of the right hemisphere without tumor overlap. Similarly, deformations within right-hemispheric functional areas are interpreted by example methods and apparatus for left cerebral GBM.

Example methods and apparatus may quantify MEDH demonstrated within different anatomical structures of the brain. For example, in one embodiment, an atlas of brain regions parcellated as anatomical structures, including deep brain structures, is non-rigidly registered with an atlas of healthy brain images, and with a set of pre-operative radiological images. The set of pre-operative radiological images may be used to train an automated classifier. Variance of voxel-wise deformation magnitudes within the anatomical structures in the set of pre-operative radiological images corresponding to the anatomical structures parcellated in the atlas of brain regions may then be used to compute MEDH for those regions. Example methods and apparatus may compute a statistical association between MEDH in particular anatomical structures and patient survival time. Example methods and apparatus may thus determine functional areas of the brain in which MEDH is associated with extreme values of survival. An extreme value of survival may be, for example, a survival time less than a threshold time period (e.g. seven months), or longer than a threshold time period (e.g. 18 months). For example, MEDH values for structures in the contralateral hemisphere may be more strongly associated with survival times than MEDH values for structures in the ipsilateral hemisphere, because structures of the ipsilateral hemisphere may overlap with tumor tissue. Structures associated with survival may include the precentral gyrus, the olfactory cortex, superior and middle frontal gyri, or parietal and temporal gyri of the contralateral hemisphere. Example methods and apparatus may also correlate MEDH values for different brain structures associated with a medium, non-extreme survival time. For example, MEDH values for medium term survival groups across different brain areas may be correlated. A medium-term, non-extreme survival time range may be for example, seven months to eighteen months.

Figure 8:
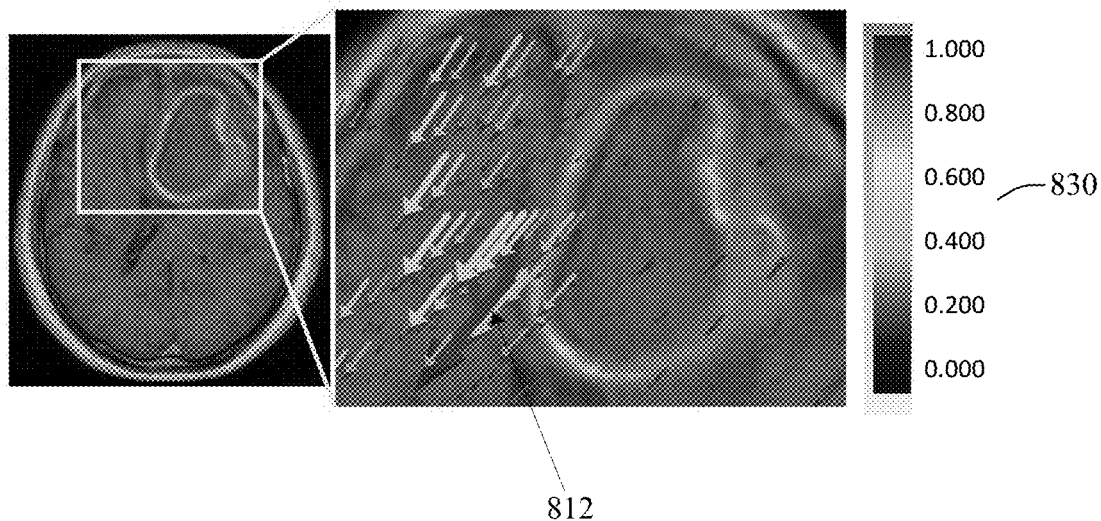
FIG. 8 illustrates deformation vectors representing tissue displacement in an image of a region of tissue demonstrating GBM.
Figure 8:
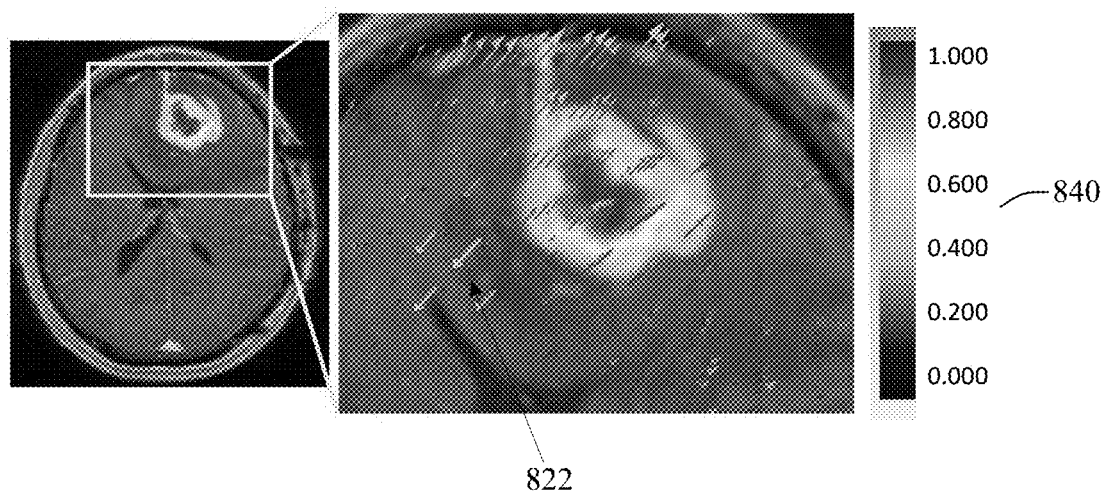

FIG. 8 illustrates deformation vectors representing tissue displacement as volume rendered 3D quivers 812 and 822 overlaid on MRI image slices 810 and 820 of right-hemispheric GBMs. In FIG. 8, deformation magnitude is proportional to the size of quivers 812 and 822. Deformation values are also represented by a grey scale. Legends 830 and 840 indicate gray scale levels for deformation values associated with quivers 812 and 822. Quivers 812 and 822 also indicate the direction of tissue displacement.

Figure 9:
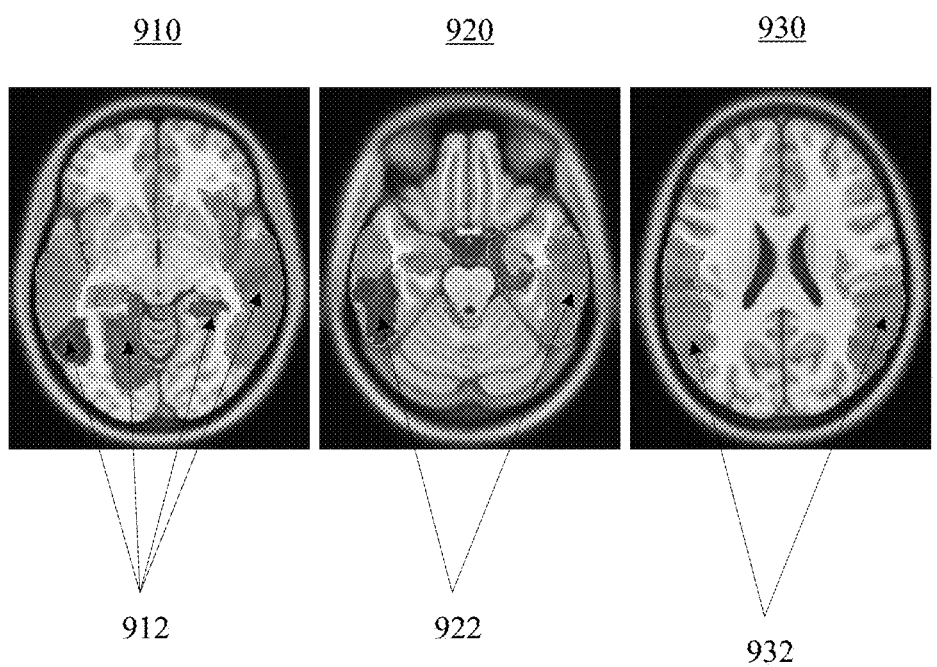
FIG. 9 illustrates brain structures with significant correlation between mass effect deformation heterogeneity and long-term and short-term GBM survival time.

FIG. 9 illustrates MRI images 910, 920, and 930 of brain structures with significant correlations between MEDH and long-term and short term GBM survival. MRI image 910 includes brain structures 912 that demonstrate high correlations between MEDH and long-term and short term GBM survival. MRI image 920 includes brain structures 922 that demonstrate high correlations between MEDH and long-term and short term GBM survival. MRI image 930 includes brain structures 932 that demonstrate high correlations between MEDH and long-term and short term GBM survival.

Figure 10:
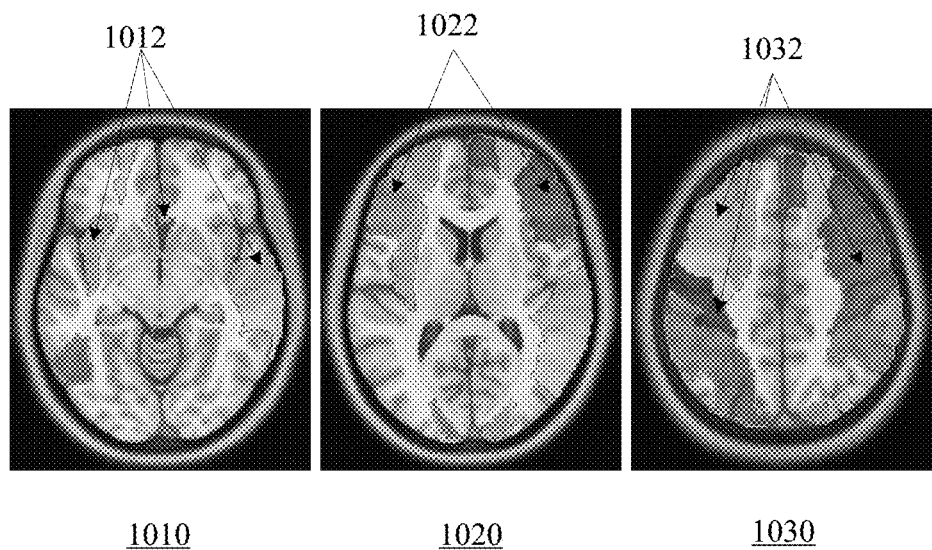
FIG. 10 illustrates brain structures with significant correlation between MEDH and medium-term GBM survival time.

FIG. 10 illustrates MRI images 1010, 1020, and 1030 of brain structures with significant correlations between MEDH and medium-term GBM survival. MRI image 1010 includes brain structures 1012 that demonstrate high correlations between MEDH and medium-term GBM survival. MRI image 1020 includes brain structures 1022 that demonstrate high correlations between MEDH and medium-term GBM survival. MRI image 1030 includes brain structures 1032 that demonstrate high correlations between MEDH and medium-term GBM survival.

Figure 11:
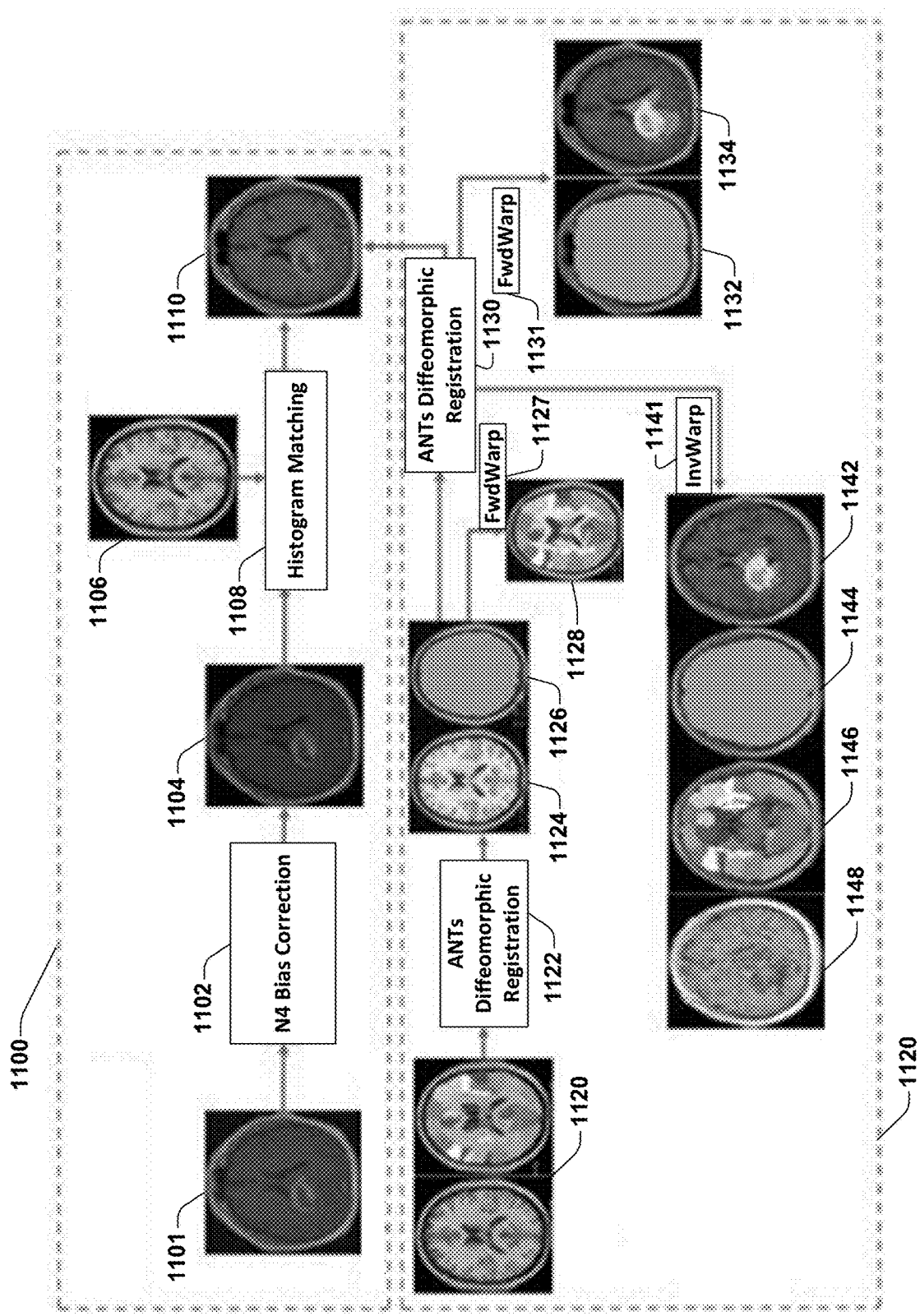
FIG. 11 is a schematic diagram of an example embodiment for computing deformation in brain tissues caused by tumor mass effect.

FIG. 11 is a schematic diagram of one possible implementation of example methods described herein. FIG. 11 illustrates a pre-processing stage 1110 and a parcellation, deformation computation, and quantification stage 1120. Pre-processing includes, at 1101, accessing a T1w MRI image of a patient demonstrating GBM. The T1w MRI image is subjected to N4 bias correction at 1102, resulting in a bias corrected image at 1104. The bias corrected image 1104 is histogram matched at 1108 with a T1w MRI image 1106 of a normal brain, resulting in a normalized patient T1w image 1110. In another embodiment, other pre-processing steps may be used.

Parcellation, deformation, and quantification stage 1120 includes accessing automated anatomical labeling (AAL) atlas T1w MRI images and brain structure parcellations 1121, which are subjected to ANTs diffeomorphic registration at 1122 with an MNI atlas 1124 and a brain mask 1126. The registered image is provided to a forward warp transformation 1127 resulting in AAL parcellations in MNI image 1128. The registered image is also subjected to ANTs diffeomorphic registration at 1130 with the patient T1w normalized image 1100, and provided to forward warp transformation 1131 resulting in patient brain mask 1132 and patient tumor mask 1134. The ANTs diffeomorphic registered image is also provide to an inverse warp transformation 1141, producing deformation map 1148, AAL parcellation map 1146, as well as brain mask 1144 and lesion mask 1142 in MNI space. A forward warp transformation, as used herein with respect to a deformable registration approach is a composite transformation of the affine (i.e., 12 degrees of freedom with 9 for rotation, scale, and sheer, with 3 for translation in the x, y, and z directions) and the voxel-wise warp or deformation field between a fixed volume or image and the moving volume or image. In this example, the fixed volume is the T1 image of the patient, and the moving volume is the MNI atlas T1 image. The forward warp transforms the T1 MNI atlas to the T1 patient image co-ordinate space. For a deformable registration, an inverse of the forward transformation exists such that it transforms the T1 patient volume to the T1 MNI atlas. Thus, the inverse warp transformation is a composite transformation of the inverse affine and inverse voxel-wise warp field between the fixed volume or image and the moving volume or image. The T1 patient image is considered as the moving volume and the MNI atlas as the fixed volume when the inverse warp transformation is applied. Example methods and apparatus may then compute a quantified difference using deformation map 448, and associated GBM survival times with different brain structures using AAL parcellation map 1146.

In another embodiment, quantifying the deformation includes computing a level of cerebrospinal fluid contraction or expansion using a tensor-based morphometry (TBM) approach. Example methods and apparatus may quantify a difference between a region of tissue demonstrating GBM and healthy brains by examining deformation changes in cerebrospinal fluid (CSF) in the cerebellum and the medial cortical surfaces at the central fissures on treatment-naïve MRI. In one embodiment, these anatomical differences are captured using TBM. TBM is a neuroimaging approach that computes a deformation field that identifies differences in relative positions of brain sub-structures across different populations with respect to a healthy template. The different populations may include long-term GBM survivors and short-term GBM survivors. In one embodiment, the different populations may include long-term, short-term, and medium-term GBM survivors.

In this embodiment using TBM, differences in relative positions of brain structures are computed as a log(Jacobian) measurement. Expansion of local brain matter relative to a healthy template may be computed as an expansion (log(Jacobian)>0), while contraction of local brain matter relative to a healthy template may be computed as a contraction (log(Jacobian)<0). Example embodiments thus quantify mass effect as manifested on anatomical MRI that differentially deforms neighboring structures in the brain, where patients with more aggressive GBM (e.g. short-survival time patients) will demonstrate higher deformations than patients with less aggressive GBM (e.g. long-survival time patients). Example methods and apparatus may classify a brain represented in an MRI image as a short-term or long-term survivor, or as a short-term, medium-term, or long-term survivor.

In this embodiment, employing a TBM approach may include creating a minimum deformation population template. The minimum deformation population template may be generated using enantiomorphic normalization. Enantiomorphic normalization may be employed to remove tumor lesions from T1w images. In another embodiment, enantiomorphic normalization may be employed with other types of images, including T2w images. Enantiomorphic normalization is a non-linear registration approach that exploits redundancy in the brain (e.g., the enantiomorphic relation between the two hemispheres) to correct a signal within a lesion using information from the undamaged homologous region within the contralateral hemisphere.

The minimum deformation population template may be used to register an image associated with a patient with the template. Example methods and apparatus may employ GLISTR to register an image with the template. In another embodiment, other registration approaches may be employed.

In this embodiment, example methods and apparatus may calculate a warp field from the registered images. The warp field may capture spatial differences between the registered images and the template. The warp field is converted to a Jacobian determinant image. The Jacobian determinant image is used in a voxel-wise two-tailed t-test with a conservative cluster-mass based family-wise error correction with a cluster forming threshold to identify areas of the brain represented in the image where deformation is associated with overall survival time. In one embodiment, the threshold is t=3.3. In another embodiment, other, different thresholds may be employed.

Example methods and apparatus may mitigate the effect of confounding variables. For example, in one embodiment, patient age may be included as a nuisance regressor in a statistical model for computing differences between the deformed brain image and the healthy brain image. In another embodiment, large deformations within a threshold distance of a tumor may be included in the statistical model as a nuisance regressor. Including age or large deformations in the statistical model as nuisance regressors mitigates the impact of age or large deformations as outliers, and increases the accuracy with which example embodiments predict GBM survival time compared to conventional approaches.

Figure 7:
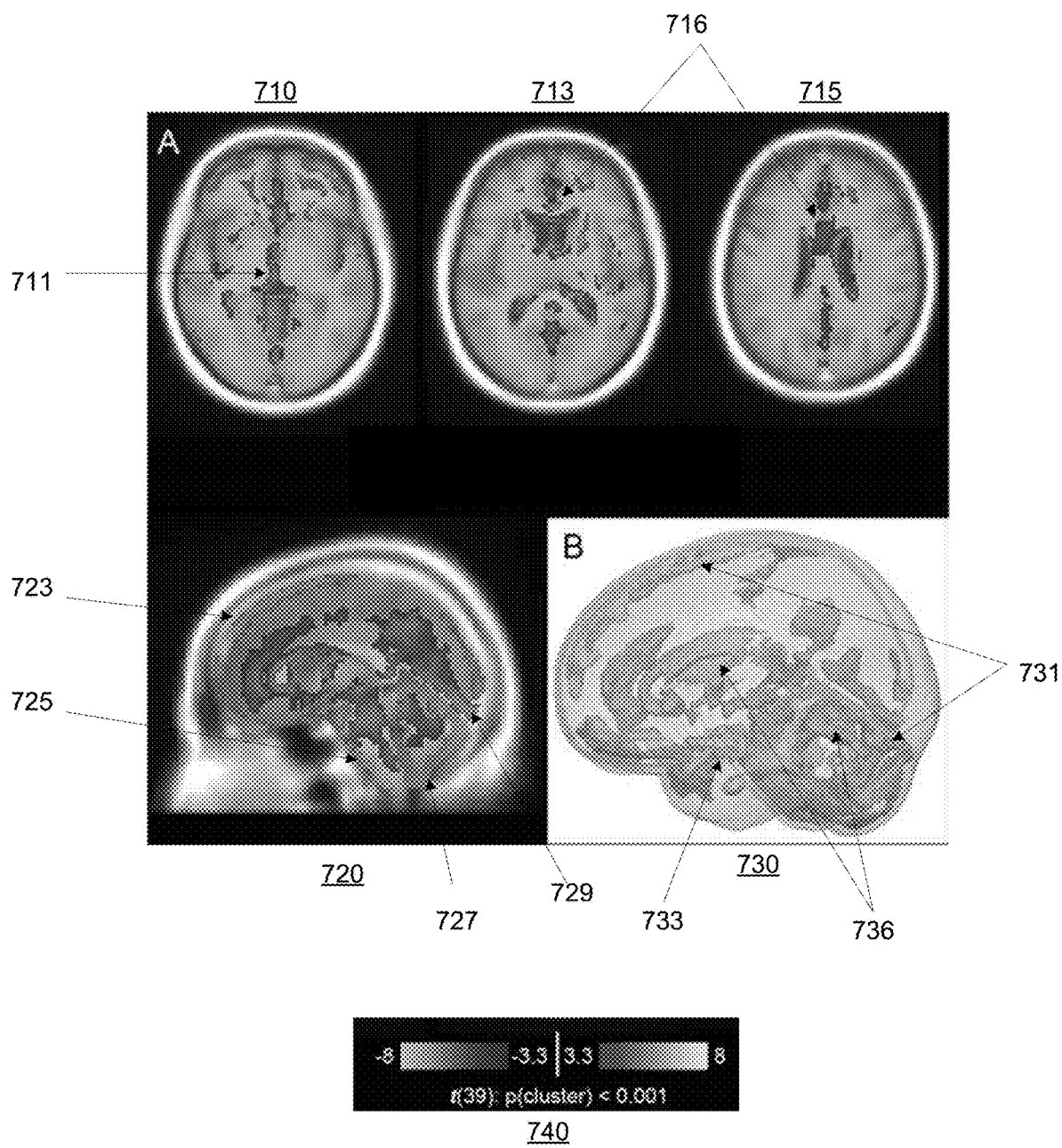
FIG. 7 illustrates a statistical comparison of tensor-based cortical deformation between long-term and short-term survival groups.

FIG. 7 illustrates per-voxel statistical quantification of tensor-based cortical deformation between long-term and short-term GBM survival groups. FIG. 7 includes a mid-sagittal view 720, along with transverse views 710, 713, and 715, of a brain demonstrating GBM as representing in an MRI image. Relative compression of CSF around the cerebellum, brainstem and cortex is represented in FIG. 7 using a grey scale. For example, relative compression of the cortex is illustrated at 723. Relative compression of the brainstem is illustrated at 725. Relative compression of the cerebellum is illustrated at 727. Relative expansion of grey matter is illustrated at 711, 716, and 729. Legend 740 indicates a gray scale corresponding to areas of compression or expansion in midsagittal view 720 and transverse views 710, 713, and 715. FIG. 7 further illustrates a three-dimensional (3D) rendering 730 of areas exhibiting different deformation between long-term and short-term survival groups. Relative compression is illustrated at 731 and 733. Relative expansion is illustrated at 736. In other embodiments, other types of scales may be employed. In one embodiment, as illustrated in FIG. 7, example methods and apparatus may quantify deformations at a per-voxel level using t-statistics cluster corrected with p(cluster)<0.001, at a conservative cluster forming threshold of t=3.3.

Example methods and apparatus may predict a survival time for a patient demonstrating GBM. A population of GBM survivors may include long-term GBM survivors and short-term GBM survivors. In one embodiment, the different populations may include long-term, short-term, and medium-term GBM survivors. Example embodiments quantify mass effect as manifested on anatomical MRI that differentially deforms neighboring structures in the brain, where patients with more aggressive GBM (e.g. short-survival time patients) will demonstrate higher deformations than patients with less aggressive GBM (e.g. long-survival time patients). Example methods and apparatus may classify a brain represented in an MRI image as a short-term or long-term survivor, or as a short-term, medium-term, or long-term survivor based, at least in part, on the quantified deformation.

Example methods and apparatus may train an automated machine learning classifier to classify a region of tissue demonstrating GBM represented in an MRI image as a long-term or short-term survivor. Training a classifier may include defining a median survival time for a population of patients demonstrating pathologically proven GBM. In one embodiment, a set of at least 40 pre-operative radiological studies including gadolinium (Gd) contrast T1w, T2w, and fluid attenuated inversion recovery (FLAIR) MRI images of patients with pathologically proven GBM are obtained. As used herein, a study includes at least one T1w, T2w, or FLAIR MRI image of a region of tissue demonstrating GBM. A median survival time for the population represented in the study may be computed. In this example, the median survival time is 15.1 months. The median survival time may be employed as a cutoff to divide the population into long-lived and short-lived sub-populations. In another embodiment, the population may be divided into long-term, medium-term, and short-term survivors.

Training a classifier may include pre-processing a member of the set of pre-operative radiological images. Pre-processing the member of the set of pre-operative radiological images may include co-registration of images from a study. Pre-processing may also include bias field correction, intensity standardization, or skull stripping. Example methods and apparatus may bias field correct the member of the set of pre-operative radiological images for intensity inhomogeneity induced by bias of the magnetic head coil using an N4 bias correction approach. Example methods and apparatus may normalize a member of the set of pre-operative radiological images using a histogram matching approach that may include, in one embodiment, 255 bins and 64 points. Example methods and apparatus may skull strip a member of the set of pre-operative radiological images using non-rigid alignment with an atlas of normal or healthy brain imagery. One atlas suitable for use with example embodiments is a T1w MNI atlas. Skull stripping may be used to obtain a patient-specific brain mask by non-rigidly aligning the atlas of normal or healthy brain imagery with the diagnostic image. Diagnostic images may also be pre-processed in a similar manner.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a circuit or a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, circuit, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Methods, apparatus, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the invention. In the figures, the thicknesses of lines, layers and/or regions may be exaggerated for clarity. Nothing in this detailed description (or drawings included herewith) is admitted as prior art.

Like numbers refer to like or similar elements throughout the description of the figures. When an element is referred to as being "connected" to another element, it can be directly connected to the other element or intervening elements may be present. In contrast, when an element is referred to as being "directly connected" to another element, there are no intervening elements present. Other words used to describe the relationship between elements should be interpreted in a like fashion (e.g., "between" versus "directly between," "adjacent" versus "directly adjacent," etc.).

FIG. 1 illustrates an example computerized method 100 for quantifying deformation differences between a radiological image of a patient demonstrating GBM and an image of a healthy brain. Method 100 includes, at 110, accessing a diagnostic image of a region of tissue demonstrating GBM pathology. Accessing the diagnostic image may include accessing an MRI image of a region of brain tissue. The MRI image may be stored, for example, in a computer memory or may be provided across a computer network. In one embodiment, the MRI image is a Gd contrast T1w, T2w, or fluid attenuated inversion recovery (FLAIR) MRI image. The diagnostic image may be acquired from an MRI system with a repetition time (TR) of 500-1800), an echo time (TE) of 5.714, or an inversion time (TI) of 785-1238 ms. The diagnostic image may be acquired with an acquisition matrix with dimensions of 256 by 192, or 320 by 224. The diagnostic image may have voxel spacing ranging from 0.468*0.468*2.5 to 0.937*0.937*5. The diagnostic image may be acquired using flip angles of 15 to 90 degrees. In another embodiment, other, different image sizes, acquisition parameters, or imaging techniques may be employed.

Method 100 also includes, at 120 generating a segmented diagnostic image from the diagnostic image. Method 100, at 120, segments a tumor region from the diagnostic image. Segmenting the tumor region includes delineating a necrotic core region, an active region, or an edema region from the background of the image. In one embodiment, the tumor region is segmented by an expert human radiologist. In another embodiment, the tumor region is segmented automatically. Segmenting the tumor region facilitates improved prediction of GBM survival time by excluding intensity differences within the tumor region which may interfere with computing deformations in regions within a threshold distance of the tumor region.

Method 100 also includes, at 130, generating a pre-processed diagnostic image by pre-processing the segmented diagnostic image. Pre-processing the segmented diagnostic image may include correcting bias-induced intensity inhomogeneity induced by a magnetic head coil used to acquire the diagnostic image. In one embodiment, an N4 bias-correction approach is employed. Pre-processing the segmented image may also include intensity normalizing the segmented diagnostic image with an atlas of MRI images representing healthy brains. The atlas of MRI images includes a healthy brain mask. Pre-processing the segmented diagnostic image may also include skull stripping the segmented diagnostic image. Skull stripping the segmented diagnostic image may include non-rigidly registering the atlas of MRI images representing healthy brains with the segmented diagnostic image. Pre-processing the segmented diagnostic image may also include generating a patient-specific brain mask using non-rigid registration. The patient-specific brain mask may be based, at least in part, on the segmented diagnostic image and the healthy brain mask.

Method 100 also includes, at 140, generating a registered diagnostic image by registering the pre-processed diagnostic image with a healthy template. Registering the pre-processed diagnostic image with the healthy template may include registering the pre-processed diagnostic image with the atlas of MRI images using a diffeomorphic registration approach. Example methods and apparatus may employ deformable registration to register the pre-processed diagnostic image with the healthy template. For example, Advanced Normalization Tools (ANTs) Symmetric Normalization (SyN) may be employed. SyN diffeomorphic registration maps brain structures in the diagnostic image to a healthy template in the presence of brain lesions. ANTs maps a tumor-exclusive region using a constrained cost-function approach that is determined by a solution of a negative tumor mask region. In another embodiment, example methods and apparatus may employ Glioma Image Segmentation and Registration (GLISTR) to register the pre-processed diagnostic image with the template. In another embodiment, other registration approaches may be employed.

Method 100 also includes, at 150, computing a quantified difference between the pre-processed diagnostic image and the healthy template. In one embodiment, computing the quantified difference between the pre-processed diagnostic image and the healthy template includes computing an MEDH value for the region of tissue. In another embodiment, computing the quantified difference includes computing the quantified difference using a TBM approach. The magnitude of the quantified difference may be associated with GBM patient survival time. For example, a higher magnitude of quantified difference may be associated with short-term survival times (e.g., less than seven months) while a lower magnitude of quantified difference may be associated with long-term survival times (e.g., more than eighteen months).

Example methods and apparatus facilitate more accurate characterization of brain cancer found in MRI images than conventional approaches. Example methods and apparatus thus improve on conventional methods by quantifying deformation differences between diagnostic images and images of healthy brains, or by characterizing a patient as likely to have a short survival time or a longer survival time, with greater accuracy and with less subjective variability than conventional methods. Example methods and apparatus therefore facilitate more judicious application of GBM therapy in a population undergoing MRI screening for GBM or other types of cancer.

Using a more appropriately determined and applied treatment may lead to less therapeutics being required for a patient or may lead to avoiding or delaying a biopsy, a resection, or other invasive procedure. When regions of cancerous tissue, including GBM tissue detected in MRI images, are more quickly and more accurately classified, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effect of improving patient outcomes.

While FIG. 1 illustrates various actions occurring in serial, it is to be appreciated that various actions illustrated in FIG. 1 could occur substantially in parallel. By way of illustration, a first process could access a diagnostic image, a second process could segment the diagnostic image, and a third process could register the diagnostic image. While three processes are described, it is to be appreciated that a greater or lesser number of processes could be employed and that lightweight processes, regular processes, threads, and other approaches could be employed.

Figure 2:
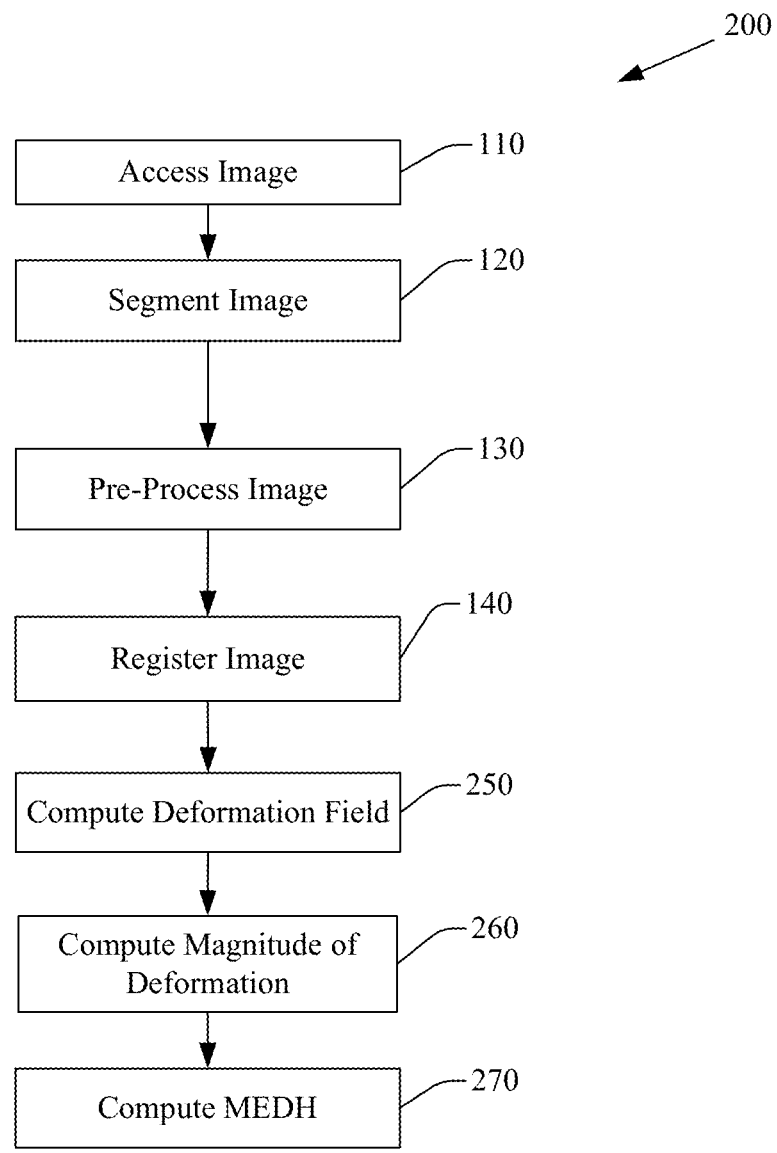
FIG. 2 illustrates an example method for quantifying deformation in an image of a region of tissue demonstrating GBM.

FIG. 2 illustrates a method 200 for quantifying deformations in an image of a region of tissue demonstrating brain cancer that is similar to method 100, but that includes additional details and actions. Method 200 includes steps 110, 120, 130, and 140 which are similar to steps 110, 120, 130, and 140 as described with respect to method 100. Method 200 also includes, at 250, computing a deformation field. Method 200 computes the deformation field based, at least in part, on the registered diagnostic image. The deformation field includes a voxel-wise deformation field vector in three planar dimensions.

Method 200 also includes, at 260, computing a magnitude of deformation. Computing the magnitude of deformation includes computing a magnitude of deformation for a voxel using a Euclidean norm of the scalar values of deformation orientations associated with the voxel-wise deformation field vector.

Method 200 also includes, at 270, computing a mass effect deformation heterogeneity (MEDH) for the region of tissue. Method 200 computes the MEDH based, at least in part, on the magnitude of deformation.

In one embodiment, method 200 may also include registering an anatomical structure atlas with the healthy template and the registered diagnostic image. In this embodiment, method 200 further includes computing an MEDH for an anatomical structure represented in the registered diagnostic image. Computing an MEDH for an anatomical structure represented in the registered diagnostic image facilitates associating MEDH with GBM survival time in a particular brain region, thus directing medical practitioners to direct time, attention, and resources to regions of the brain that may benefit from treatment more than other regions.

Example methods and apparatus facilitate quantifying higher variations in tissue deformation within the functionally eloquent and memory areas of the contralateral cerebral hemisphere and relating those variations with decreased survival in GBM. Example methods and apparatus measure brain tissue displacements caused by GBM in the cortical and subcortical structures by non-rigidly aligning post contrast T1-weighted MRI to a healthy brain atlas. Example methods and apparatus measure variance of voxel-wise tissue deformation magnitudes as quantified by MEDH within the brain structures. In one embodiment, the MEDH is correlated with overall GBM survival on a total of 89 subjects with primary tumors on the right (n=41) and left (n=48) cerebral hemispheres. Decreased survival time is associated with increased MEDH in areas of language comprehension, social cognition, visual perception, emotion, somato-sensory, cognitive and motor-control functions ($r > 0.40$, $p < 0.05$) and in the memory areas ($r > 0.50$, $p < 0.05$) in the left cerebral hemisphere. Higher MEDH in functionally eloquent areas of the left cerebral hemisphere due to GBM in the right cerebral hemisphere is associated with poor survival.

Example methods and apparatus facilitate quantifying MEDH correlation with survival time. For right-hemispheric tumor groups, MEDH in functional areas is negatively correlated with statistical significance ($p < 0.05$) with survival across both hemispheres. Structures in the contralateral hemisphere may be more relevant for the analysis because the structures of ipsilateral hemisphere may overlap with the tumor representation for the group. Right hemispheric patients may exhibit a large degree of midline shift for the right-hemispheric tumors compared to left-hemispheric tumors. Hence, for right-hemispheric tumors, the MEDH in contralateral functional areas is significantly associated with long, short and medium-term survival. Table 1 illustrates significant correlation values for long-term and short-term survival groups. In table 1, AAL regions of the right cerebral tumor groups, within which MEDH may be negatively correlated with long-term and short-term survival. The left-hemispheric structures of significance may be more relevant. The correlation is shown as r and the significance ($p < 0.05$) as p.

TABLE 1

| Left Hemisphere | | | Right Hemisphere | | |
|---|---|---|---|---|---|
| Region | r | p | Region | r | p |
| Hippocampus | −0.43 | 0.034 | Olfactory Cortex | −0.41 | 0.045 |
| Lingual G | −0.47 | 0.018 | Insula | −0.43 | 0.034 |
| Postcentral G | −0.42 | 0.036 | Parahippocampal G | −0.50 | 0.011 |
| Supramarginal G | −0.46 | 0.021 | Supramarginal G | −0.40 | 0.048 |
| Superior Temporal G | −0.42 | 0.039 | Superior Temporal G | −0.43 | 0.031 |
| Middle Temporal G | −0.43 | 0.035 | Middle Temporal G | −0.45 | 0.025 |
| Inferior Temporal G | −0.55 | 0.005 | Inferior Temporal G | −0.43 | 0.03 |
| Heschl G | −0.53 | 0.006 | | | |
| Cerebellum 3 | −0.45 | 0.042 | | | |
| Cerebellum 9 | −0.41 | 0.045 | | | |
| Vermis 3 (non-hemispheric) | −0.41 | 0.046 | | | |

Table 2 illustrates correlation values for a medium-term survival group. In table 2, AAL regions of the right cerebral tumor groups, within which the MEDH are negatively correlated with medium-term survival, are presented. The left-hemispheric regions of significance may be more relevant. The correlation is shown as r and the significance ($p<0.05$) as p.

TABLE 2

| | Left Hemisphere | | | Right Hemisphere | | |
|---|---|---|---|---|---|---|
| Region | r | p | Region | r | p |
| Precentral G | −0.49 | 0.046 | Precentral G | −0.63 | 0.006 |
| Sup Frontal DorsoLateral | −0.55 | 0.023 | Sup Frontal DorsoLateral | −0.52 | 0.032 |
| Middle Frontal G | −0.54 | 0.026 | Middle Frontal G | −0.67 | 0.003 |
| Inf Frontal G Tri Part | −0.57 | 0.016 | Inf Frontal G Tri Part | −0.62 | 0.007 |
| Olfactory Cortex | −0.53 | 0.028 | Olfactory Cortex | −0.68 | 0.002 |
| Sup Occipital G | −0.60 | 0.010 | Sup Occipital G | −0.51 | 0.034 |
| Postcentral G | −0.73 | 0.0008 | Postcentral G | −0.63 | 0.006 |
| Inf Parietal G | −0.58 | 0.013 | Inf Parietal G | −0.58 | 0.018 |
| Sup Frontal G Orbital Part | −0.50 | 0.039 | Inf Frontal G Opercular Part | −0.66 | 0.003 |
| Insula | −0.52 | 0.031 | Sup Frontal G Medial | −0.66 | 0.003 |
| Sup Parietal G | −0.63 | 0.003 | Gyrus Rectus | −0.55 | 0.003 |
| Inf Temporal G | −0.60 | 0.01 | Cuneus | −0.56 | 0.019 |
| Temporal Pole Middle Temporal G | −0.53 | 0.028 | Supramarginal G | −0.54 | 0.025 |
| Vermis 3 (non-hemispheric) | −0.65 | 0.004 | Sup Temporal G | −0.52 | 0.032 |
| | | | Middle Temporal G | −0.48 | 0.048 |

MEDH in AAL regions due to mass effect is associated with survival for right-hemispheric tumors. Specific functional areas within which MEDH is associated with survival in general, are the precentral gyrus, olfactory cortex, superior and middle frontal gyri, parietal and the temporal gyri of the contralateral hemisphere. Increased MEDH within the left hippocampus and Heschl gyrus is also associated with poor survival. In all survival groups, a commonality exists in the association of MEDH in left postcentral gyrus and cerebellar vermis with survival times. Table 1 and Table 2 show detailed lists of AAL regions in which the MEDH negatively correlates with extreme ends (e.g. long-term and short-term) of survival and medium-term survival respectively with statistical significance ($p<0.05$). Example methods and apparatus facilitate the interpretation of MEDH in significantly correlated left-hemispheric structures since the deformation in these regions is exclusive of tumor areas.

Figure 3:
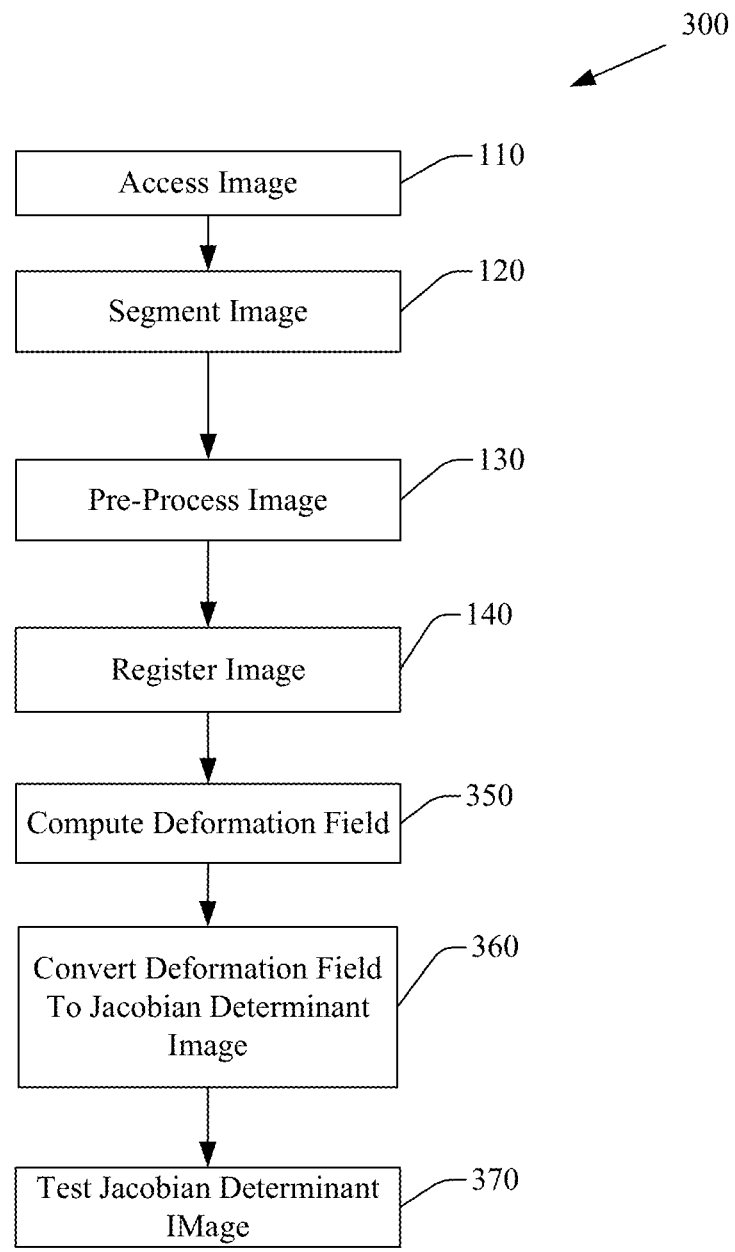
FIG. 3 illustrates an example method for quantifying deformation in an image of a region of tissue demonstrating GBM.

FIG. 3 illustrates a method 300 for quantifying deformations in an image of a region of tissue demonstrating brain cancer that is similar to method 100, but that includes additional details and actions for computing the quantified difference using a TBM approach. Method 300 includes steps 110, 120, 130, and 140 which are similar to steps 110, 120, 130, and 140 as described with respect to method 100 and method 200. Method 300 also includes, at 350, computing a deformation field. The deformation field is based, at least in part, on the registered diagnostic image. The deformation field identifies a set of differences in a relative position of a brain sub-structure represented in the registered diagnostic image relative to the position of the brain sub-structure represented in the healthy template. A member of the set of differences represents an expansion of local brain matter or a contraction of local brain matter.

Method 300 also includes, at 360, converting the deformation field to a Jacobian determinant image. Differences in relative positions of brain structures are computed as a log(Jacobian) measurement. Expansion of local brain matter relative to a healthy template may be computed as an expansion (log(Jacobian)>0), while contraction of local brain matter relative to a healthy template may be computed as a contraction (log(Jacobian)<0).

Method 300 also includes, at 370, performing a voxel-wise two-tailed t-test using the Jacobian determinant image. The voxel-wise two-tailed t-test employs cluster-mass-based family-wise error correction and a cluster forming threshold. In one embodiment, the cluster forming threshold value is 3.3. In other embodiments, other threshold values may be employed. Performing the voxel-wise two-tailed t-test using the Jacobian determinant image facilitates identifying areas of the brain where deformation is associated significantly with overall survival time.

Embodiments of example methods and apparatus may also include providing the registered diagnostic image to an automated classifier. Providing the registered diagnostic image to the automated classifier may include providing the registered diagnostic image across a computer network. In one embodiment, the automated classifier is a machine learning classifier, including a support vector machine (SVM) classifier, a quadratic discriminant analysis (QDA) classifier, a linear discriminant analysis (LDA) classifier, or a random forest classifier.

In one embodiment, the automated classifier classifies the registered diagnostic image using a TBM approach. Classifying the registered diagnostic image using a TBM approach includes computing a deformation field. In another embodiment, the automated classifier computes an MEDH score for the registered diagnostic image. The MEDH score may be computed for a particular anatomical structure of the brain represented in the registered diagnostic image. The particular anatomical structure may be defined, for example, by an atlas of anatomical regions registered with the registered diagnostic image.

Example methods and apparatus may also include receiving, from the automated classifier, a classification of the registered diagnostic image. The automated classifier may classify the registered diagnostic image as a short-lived region or a long-lived region based, at least in part, on the deformation field, or the MEDH score.

Example methods and apparatus may also include controlling a computer aided diagnostic (CADx) system to compute a probability of survival for the patient. The probability of survival may be based, at least in part, on the classification. The probability of survival may also be based on the registered diagnostic image, the set of differences, the quantified difference, or the MEDH score. In one embodiment, the CADx system generates a personalized GBM treatment plan based, at least in part, on the probability of survival.

Example methods and apparatus may train an automated classifier. Training the automated classifier may include accessing a set of pre-operative radiological images of a region of tissue demonstrating GBM. The set of pre-operative radiological images are acquired from a population of patients that experienced pathologically proven GBM. Members of the population have a survival time. In one embodiment, the population includes at least 40 patients demonstrating pathologically proven GBM. A member of the population may demonstrate left hemisphere GBM or right hemisphere GBM. A member of the set of pre-operative radiological images may be a Gd contrast T1w, T2w, or a FLAIR MRI image.

Training the automated classifier may include computing a median survival time for the population. Training automated classifier may include defining a short-lived set and a long-lived set based, at least in part, on the median survival time. For example, members of the population having a survival time less than the median survival time may be sorted into the short-lived set, while members of the population having a survival time greater than the median survival time may be sorted into the long-lived set. Other numbers of sets may be employed. In one embodiment, a short-lived set, a medium-lived set, and a long-lived set may be defined. For example, the short lived set may have a survival time of less than seven months, the medium-lived set may have a survival time of seven months to eighteen months, and the long-lived set may have a survival time of more than eighteen months.

Training the automated classifier may include generating a registered set of images by registering the pre-processed set. In one embodiment, non-rigid registration is employed. In another embodiment, other registration techniques or approaches may be employed.

Training the automated classifier may include identifying a deformation area of tissue represented in a member of the registered set. The deformation area is associated with survival time. For example, deformation in a first region (e.g. precentral gyrus, olfactory cortex, superior and middle frontal gyri, or other anatomical brain structure) may be associated with different survival times. In one embodiment, the registered set is also registered with an atlas of brain anatomical regions. Registering the registered set with the atlas of brain anatomical regions facilitates identifying regions within the brain that may be associated with survival time when subjected to threshold levels of MEDH.

In one embodiment, identifying the deformation area of tissue includes generating a warp field based on the registration. Identifying the deformation area of tissue further includes converting the warp field to a Jacobian determinant image. Identifying the deformation area of tissue further includes performing a voxel-wise two-tailed t-test using the Jacobian determinant image.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, method 300, and method 1200. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 4:
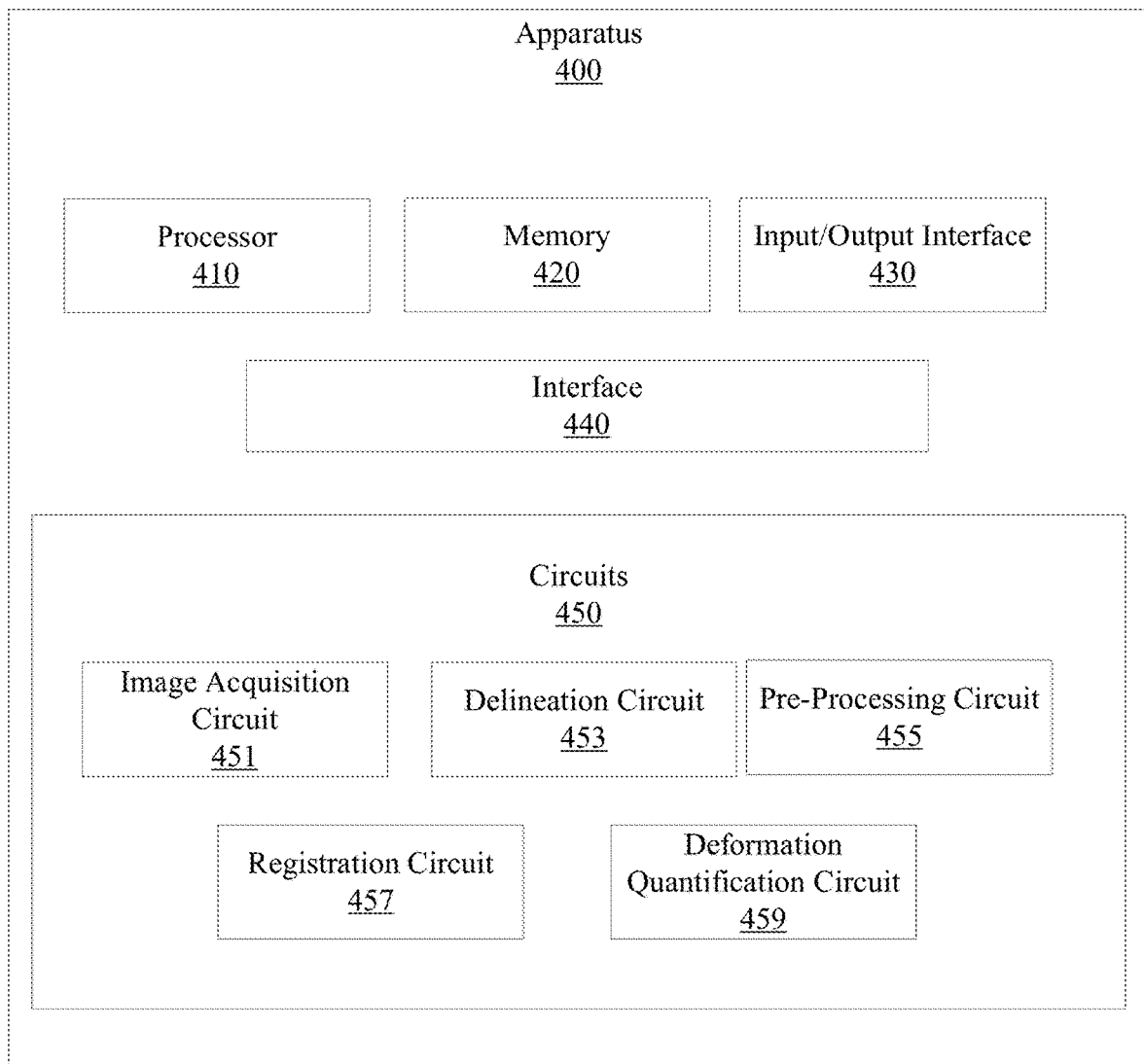
FIG. 4 illustrates an example apparatus that quantifies deformation in an image of a region of tissue demonstrating GBM.

FIG. 4 illustrates an example apparatus 400 for quantifying deformation in an image of a region of tissue demonstrating GBM. Apparatus 400 may also classify a region of tissue demonstrating GBM represented in an MRI image as a short-term survivor or a long-term survivor. Apparatus 400 includes a processor 410, a memory 420 that stores a template image of a healthy brain, an input/output (I/O) interface 430, a set of circuits 450, and an interface 440 that connects the processor 410, the memory 420, the I/O interface 430, and the set of circuits 450. The set of circuits 450 includes an image acquisition circuit 451, a delineation circuit 453, a pre-processing circuit 455, a registration circuit 457, and a deformation quantification circuit 459. In one embodiment, the functionality associated with the set of circuits 450 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 450 are implemented as ASICs or SOCs.

Image acquisition circuit 451 acquires a radiological image of region of tissue demonstrating GBM. The image may be acquired from, for example, an MRI apparatus. The region of tissue may be a section of tissue demonstrating cancerous pathology in a patient. The image of the region of tissue may include an image of a brain, or of anatomical structures of a brain. In one embodiment, the image is a Gd contrast T1w, T2w, or FLAIR MRI image. The image may be acquired from an MRI system with TR/TE/TI of 500-1800/5.714/785-1238 ms. The image may be acquired with an acquisition matrix of 256 by 192 or 320 by 224. The diagnostic image may have voxel spacing ranging from 0.468*0.468*2.5 to 0.937*0.937*5. The image may be acquired using flip angles of 15 to 90 degrees. Other imaging approaches may be used to generate and access the image accessed by image acquisition circuit 451.

Delineation circuit 453 generates a segmented image by segmenting a tumor region represented in the image from the background of the image. Delineation circuit 453 may segment a combined tumor region by delineating a necrotic core region, an active region, or an edema region from the background of the image.

Pre-processing circuit 455 generates a pre-processed image by pre-processing the segmented image. Pre-processing the segmented image may include intensity normalizing the segmented diagnostic image with an atlas of MRI images representing healthy brains. The atlas of MRI images may include a healthy brain mask. Pre-processing circuit 455 may also pre-process the segmented image by skull stripping the segmented diagnostic image. Pre-processing circuit 455 may skull strip the segmented diagnostic image by non-rigidly registering the atlas of MRI images representing healthy brains with the segmented diagnostic image. Pre-processing circuit 455 may also pre-process the segmented image by generating a patent-specific brain mask based, at least in part, on the segmented diagnostic image and the healthy brain mask.

Registration circuit 457 generates a registered image by registering the segmented image with the template image. Registration circuit 457 may register the segmented image with a template image or with an atlas of MRI images of healthy brains using a diffeomorphic registration approach. In another embodiment, registration circuit 457 may employ other registration approaches, including GLISTR.

Deformation quantification circuit 459 computes a set of differences between a position of a brain sub-structure represented in the registered image relative to the position of the brain sub-structure represented in the template image. In one embodiment, deformation quantification circuit 459 computes the set of differences by computing an MEDH score. The MEDH score is based on a deformation field that represents a difference in a relative position of the brain sub-structure represented in the registered image from the position of the sub-structure represented in an image of a long-term survival brain or the position of the sub-structure represented in an image of a short-term survival brain. The deformation field is computed voxel-wise in three planar orientations.

In another embodiment, the deformation quantification circuit 459 computes the set of differences using a TBM approach. Deformation quantification circuit 459 computes a warp field from the registered set. Deformation quantification circuit 459 generates a Jacobian determinant image based on the warp field, performing a voxel-wise two-tailed t-test using the Jacobian determinant image. In one embodiment, the voxel-wise two-tailed t-test employs cluster-mass-based family-wise error correction and a cluster forming threshold. Deformation quantification circuit 459 identifies a deformation in the brain sub-structure represented in the Jacobian determinant image.

Figure 5:
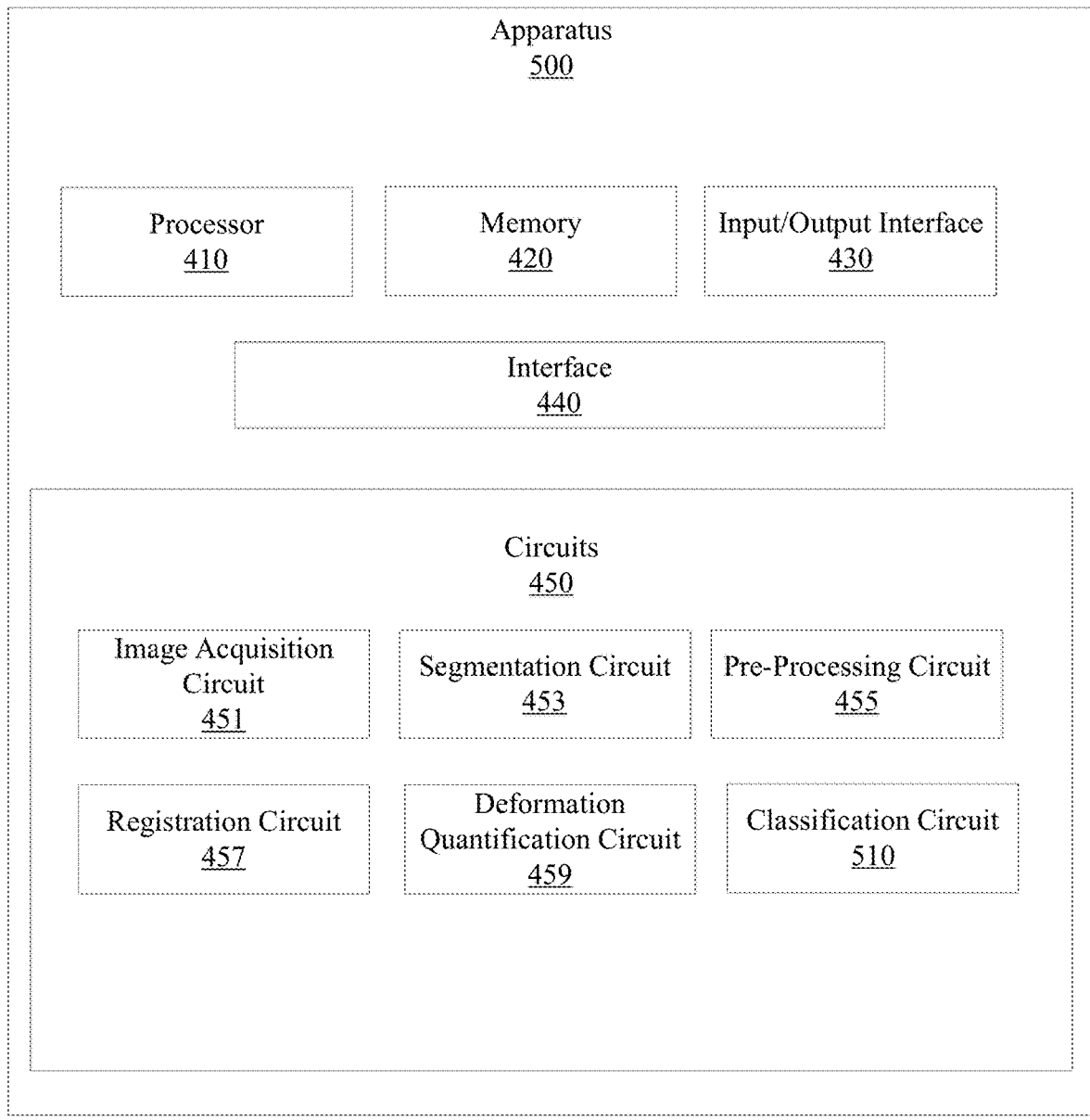
FIG. 5 illustrates an example apparatus that quantifies deformation in an image of a region of tissue demonstrating GBM.

FIG. 5 illustrates an apparatus 500 that is similar to apparatus 400 but that includes additional elements and details. Apparatus 500 includes a classification circuit 510 that classifies the region of tissue as a long-term survivor or a short-term survivor based, at least in part, on the set of differences and the brain sub-structure. Classification circuit 510 may classify the region of tissue using QDA, LDA, random forests, or other machine learning approaches or analytical techniques.

In another embodiment, classification circuit 510 may control a CADx system to classify the image based, at least in part, on the classification. For example, classification circuit 510 may control a brain cancer CADx system to classify the image based, at least in part, on the set of differences, the MEDH score, and the brain sub-structure. In other embodiments, other types of CADx systems may be controlled, including CADx systems for classifying other types of cancer tumors and other diseases where disease prognosis prediction may be based on a set of quantified differences between structures represented in MRI images of pathological tissue and healthy tissue.

In another embodiment, apparatus 400 or apparatus 500 may include a display circuit. The display circuit generates a quantitative statistical map of the radiological image. The quantitative statistical map displays differences between the radiological image and the template image or atlas of healthy brain images. In one embodiment, the quantitative statistical map represents areas in the radiological image that demonstrate increased volume, or areas that demonstrate relative compression of cerebrospinal fluid. In another embodiment, the quantitative statistical map represents MEDH scores associated with brain structures represented in the radiological image. The display circuit displays the quantitative statistical map, the radiological image, the set of differences, the brain structures, or the MEDH score on a display device. In one embodiment, the display circuit may control the CADx system to display the quantitative statistical map, the radiological image, the brain structures, the MEDH score, or the set of differences on a computer monitor, a smart phone display, a tablet display, or other displays. Displaying the quantitative statistical map, the radiological image, the brain structures, the MEDH score, or the set of differences may also include printing the quantitative statistical map, the radiological image, the brain structures, the MEDH score, or the set of differences. Display circuit 553 may also control the CADx to display an image of the region of tissue demonstrating a brain tumor. By displaying the quantitative statistical map, the radiological image, the brain structures, the MEDH score, or the set of differences, example apparatus provide a timely and intuitive way for a human radiologist to more accurately classify a patient as a long-term or short-term survivor, thus improving on conventional approaches to predicting cancer recurrence and disease progression.

Figure 6:
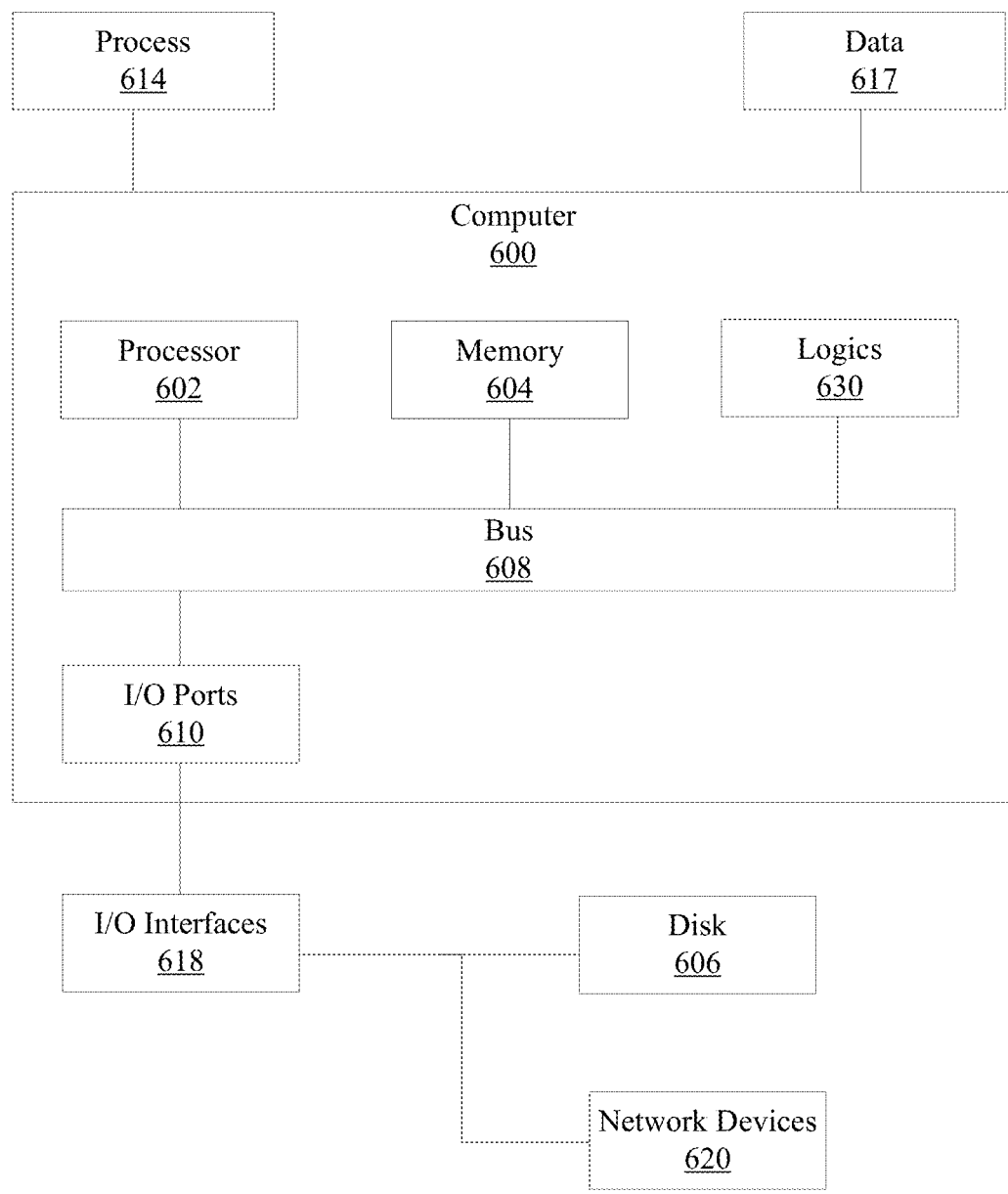
FIG. 6 illustrates an example computer in which example methods and apparatus described herein may operate.

FIG. 6 illustrates an example computer 600 in which example methods illustrated herein can operate and in which example circuits or logics may be implemented. In different examples, computer 600 may be part of an MRI system, may be operably connectable to an MRI system, or may be part of a CADx system.

Computer 600 includes a processor 602, a memory 604, and input/output (I/O) ports 610 operably connected by a bus 608. In one example, computer 600 may include a set of logics 630 that perform a method for predicting survival time for a patient demonstrating GBM. Thus, the set of logics 630, whether implemented in computer 600 as hardware, firmware, and/or a combination thereof may provide means (e.g., hardware, firmware) for predicting survival time for a patient demonstrating GBM. In different examples, the set of logics 630 may be permanently and/or removably attached to computer 600. In one embodiment, the functionality associated with the set of logics 630 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 630 are implemented as ASICs or SOCs.

Processor 602 can be a variety of various processors including dual microprocessor and other multi-processor architectures. Memory 604 can include volatile memory and/or non-volatile memory. A disk 606 may be operably connected to computer 600 via, for example, an input/output interface (e.g., card, device) 618 and an input/output port 610. Disk 606 may include, but is not limited to, devices like a magnetic disk drive, a tape drive, a Zip drive, a flash memory card, or a memory stick. Furthermore, disk 606 may include optical drives like a CD-ROM or a digital video ROM drive (DVD ROM). Memory 604 can store processes 614 or data 617, for example. Disk 606 or memory 604 can store an operating system that controls and allocates resources of computer 600.

Bus 608 can be a single internal bus interconnect architecture or other bus or mesh architectures. While a single bus is illustrated, it is to be appreciated that computer 600 may communicate with various devices, logics, and peripherals using other busses that are not illustrated (e.g., PCIE, SATA, Infiniband, 1394, USB, Ethernet).

Computer 600 may interact with input/output devices via I/O interfaces 618 and input/output ports 610. Input/output devices can include, but are not limited to, digital whole slide scanners, an optical microscope, a keyboard, a microphone, a pointing and selection device, cameras, video cards, displays, disk 606, network devices 620, or other devices. Input/output ports 610 can include but are not limited to, serial ports, parallel ports, or USB ports.

Computer 600 may operate in a network environment and thus may be connected to network devices 620 via I/O interfaces 618 or I/O ports 610. Through the network devices 620, computer 600 may interact with a network. Through the network, computer 600 may be logically connected to remote computers. The networks with which computer 600 may interact include, but are not limited to, a local area network (LAN), a wide area network (WAN), or other networks.

Figure 12:
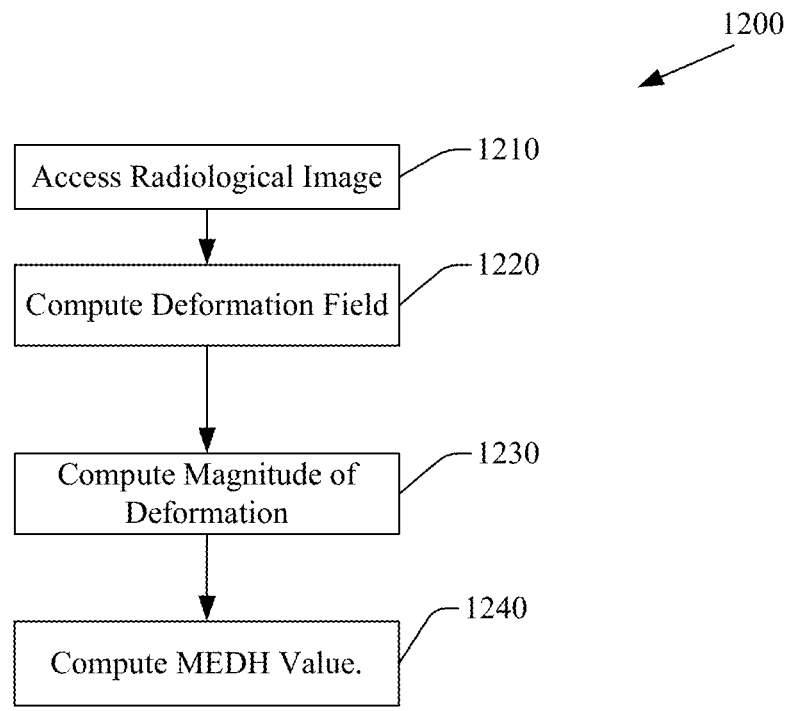
FIG. 12 illustrates an example method for computing a mass effect deformation heterogeneity value for an image of a region of tissue demonstrating GBM.

FIG. 12 illustrates an example methods 1200 for quantifying MEDH in region of tissue demonstrating GBM. Method 1200 includes, at 1210, accessing a radiological image of the region of tissue. The radiological image may be an MRI image. The radiological image includes a plurality of voxels, or a plurality of pixels.

Method 1200 also includes, at 1220, computing a deformation field by registering the radiological image with an atlas of images of healthy regions of tissue. The deformation field includes a voxel-wise deformation field vector in three planar dimensions. The deformation field expresses differences between the radiological image and the atlas images of healthy regions of tissue caused by mass effect deformation.

Method 1200 also includes, at 1230, computing a magnitude of deformation for a voxel. The voxel is a member of the plurality of voxels. Method 1200 computes the magnitude of deformation using a Euclidean norm of the scalar values of deformation orientations associated with the voxel-wise deformation field vector.

Method 1200 also includes, at 1240, computing an MEDH value for the region of tissue. The MEDH value expresses the mass effect deformation heterogeneity of a brain structure. The MEDH value is based, at least in part, on the magnitude of deformation. The MEDH value may be associated with a parcellated region associated with a brain structure represented in the radiological image registered with an atlas of brain structures. In one embodiment, the atlas is an AAL atlas with one hundred and sixteen parcellated regions.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another circuit, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed by a computer control the computer to perform a method, the method comprising:
   accessing a diagnostic image of a region of tissue in a patient demonstrating glioblastoma multiforme (GBM) pathology;
   generating a segmented diagnostic image by segmenting a tumor region from the diagnostic image;
   generating a pre-processed diagnostic image by pre-processing the segmented diagnostic image, where pre-processing the segmented diagnostic image includes correcting bias-induced intensity inhomogeneity using an N4 bias-correction approach;
   generating a registered diagnostic image by registering the pre-processed diagnostic image with a healthy template; and
   computing a quantified difference between the pre-processed diagnostic image and the healthy template.

2. The non-transitory computer-readable storage device of claim 1, where pre-processing the segmented diagnostic image includes intensity normalizing the segmented diagnostic image with an atlas of MRI images representing healthy brains, where the atlas of MRI images includes a healthy brain mask.

3. The non-transitory computer-readable storage device of claim 2, where pre-processing the segmented diagnostic image includes skull stripping the segmented diagnostic image by non-rigidly registering the atlas of MRI images representing healthy brains with the segmented diagnostic image.

4. The non-transitory computer-readable storage device of claim 3, where pre-processing the segmented diagnostic image includes generating a patent-specific brain mask based, at least in part, on the segmented diagnostic image and the healthy brain mask.

5. The non-transitory computer-readable storage device of claim 4, where registering the pre-processed diagnostic image includes registering the pre-processed diagnostic image with the atlas of MRI images using a diffeomorphic registration approach or a Glioma Image Segmentation and Registration (GLISTR) approach.

6. The non-transitory computer-readable storage device of claim 5, where computing the quantified difference between the pre-processed diagnostic image and the healthy template comprises computing the quantified difference using a tensor-based morphometry (TBM) approach.

7. The non-transitory computer-readable storage device of claim 6, where computing the quantified difference using the TBM approach comprises:
    computing a deformation field based, at least in part, on the registered diagnostic image, where the deformation field identifies a set of differences in a relative position of a brain sub-structure represented in the registered diagnostic image relative to the position of the brain sub-structure represented in the healthy template, where a member of the set of differences represents an expansion of local brain matter or a contraction of local brain matter;
    converting the deformation field to a Jacobian determinant image; and
    performing a voxel-wise two-tailed t-test using the Jacobian determinant image, where the voxel-wise two-tailed t-test employs cluster-mass-based family-wise error correction and a cluster forming threshold.

8. The non-transitory computer-readable storage device of claim 7, where the cluster forming threshold is 3.3.

9. The non-transitory computer-readable storage device of claim 5, where computing the quantified difference between the pre-processed diagnostic image and the healthy template comprises:
    computing a deformation field based, at least in part, on the registered diagnostic image, where the deformation field includes a voxel-wise deformation field vector in three planar dimensions;
    computing a magnitude of deformation for a voxel using a Euclidean norm of scalar values of deformation orientations associated with the voxel-wise deformation field vector; and
    computing a mass effect deformation heterogeneity (MEDH) value for the region of tissue based, at least in part, on the magnitude of deformation.

10. The non-transitory computer-readable storage device of claim 9, the method further comprising:
    registering an anatomical structure atlas with the healthy template and the registered diagnostic image; and
    computing an MEDH value for an anatomical structure represented in the registered diagnostic image.

11. The non-transitory computer-readable storage device of claim 1, where the diagnostic image is a gadolinium (Gd) contrast T1w, T2w, or fluid attenuated inversion recovery (FLAIR) magnetic resonance imaging (MRI) image.

12. The non-transitory computer-readable storage device of claim 1, where segmenting the tumor region includes delineating a necrotic core region, an active region, or an edema region from the background of the image.

13. The non-transitory computer-readable storage device of claim 1, the method further comprising:
    calculating an association between the quantified difference and a patient survival time;
    computing a probability of survival based, at least in part, on the quantified difference or the association; and
    controlling a CADx system to generate a personalized GBM treatment plan for the patient based, at least in part, on the quantified difference.

14. A method for quantifying mass effect deformation heterogeneity (MEDH) in region of tissue demonstrating Glioblastoma Multiforme, the method comprising:
    accessing a radiological image of the region of tissue, where the radiological image includes a plurality of voxels;
    computing a deformation field by registering the radiological image with an atlas of images of healthy regions of tissue, where the deformation field includes a voxel-wise deformation field vector in three planar dimensions;
    computing a magnitude of deformation for a member of the plurality of voxels using a Euclidean norm of scalar values of deformation orientations associated with the voxel-wise deformation field vector; and
    computing an MEDH value for the region of tissue based, at least in part, on the magnitude of deformation.

* * * * *